US008971936B2

(12) United States Patent
Derchak

(10) Patent No.: US 8,971,936 B2
(45) Date of Patent: Mar. 3, 2015

(54) MULTIMODAL METHOD AND SYSTEM FOR TRANSMITTING INFORMATION ABOUT A SUBJECT

(75) Inventor: P. Alexander Derchak, Oxnard, CA (US)

(73) Assignee: adidas AG, Herzogenaurach (DE)

( * ) Notice: Subject to any disclaimer, the term of this patent is extended or adjusted under 35 U.S.C. 154(b) by 465 days.

(21) Appl. No.: 12/869,592

(22) Filed: Aug. 26, 2010

(65) Prior Publication Data

US 2011/0054270 A1    Mar. 3, 2011

Related U.S. Application Data

(60) Provisional application No. 61/275,587, filed on Sep. 1, 2009.

(51) Int. Cl.
*H04B 1/00* (2006.01)
*H04B 15/00* (2006.01)
(Continued)

(52) U.S. Cl.
CPC .............. *A61B 5/1135* (2013.01); *A61B 5/0002* (2013.01); *A61B 5/02055* (2013.01); *A61B 5/411* (2013.01); *A61B 5/6805* (2013.01); *G06F 19/3481* (2013.01); *A61B 5/02438* (2013.01); *A61B 5/0402* (2013.01); *A61B 5/0476* (2013.01); *A61B 5/0488* (2013.01); *A61B 5/11* (2013.01); *A61B 5/14551* (2013.01); *A61B 7/00* (2013.01);
(Continued)

(58) Field of Classification Search
CPC ......... H04B 1/005; H04B 7/02; A61B 5/0004

USPC ........ 455/41.2, 41.3, 500, 66.1, 67.11, 552.1, 455/553.1, 575.6, 90.1, 91, 100, 101
See application file for complete search history.

(56) References Cited

U.S. PATENT DOCUMENTS

| | | | |
|---|---|---|---|
| 3,831,586 A | 8/1974 | Petit | |
| 4,033,332 A | 7/1977 | Hardway et al. | |

(Continued)

FOREIGN PATENT DOCUMENTS

| | | | |
|---|---|---|---|
| WO | WO 01/28420 A1 | 4/2001 | |
| WO | WO 01/76467 A2 | 10/2001 | |

(Continued)

OTHER PUBLICATIONS

Badler, et al., "Simulating Humans: Computer Graphics, Animation, and Control", (New York: Oxford Univeristy Press, 1993).

(Continued)

*Primary Examiner* — Andrew Wendell
(74) *Attorney, Agent, or Firm* — Sterne, Kessler, Goldstein & Fox P.L.L.C.

(57) ABSTRACT

The present invention is directed to multimodal communications means for transmitting signals representing physiological, performance, and contextual information associated with a subject. In an exemplary embodiment, the multimodal communications means includes multiple radio subsystems (or modes) that enable connection to an external monitoring device to be acquired in a wide range of settings where a single radio mode would be ineffective. Additionally, combining the multimodal communications means of the invention with real-time data-processing allows the communications functionality to be engaged only when data determined to be relevant to the user is identified.

30 Claims, 8 Drawing Sheets

(51) Int. Cl.

| | | |
|---|---|---|
| *H04B 1/38* | (2006.01) | |
| *H04B 7/00* | (2006.01) | |
| *A61B 5/113* | (2006.01) | |
| *A61B 5/00* | (2006.01) | |
| *A61B 5/0205* | (2006.01) | |
| *G06F 19/00* | (2011.01) | |
| *A61B 5/024* | (2006.01) | |
| *A61B 5/0402* | (2006.01) | |
| *A61B 5/0476* | (2006.01) | |
| *A61B 5/0488* | (2006.01) | |
| *A61B 5/11* | (2006.01) | |
| *A61B 5/1455* | (2006.01) | |
| *A61B 7/00* | (2006.01) | |

(52) U.S. Cl.
CPC ......... *A61B 7/003* (2013.01); *A61B 2562/0219* (2013.01)
USPC ................... 455/500; 455/90.1; 455/66.1

(56) References Cited

U.S. PATENT DOCUMENTS

| | | | |
|---|---|---|---|
| 4,258,718 A | 3/1981 | Goldman | |
| 4,267,845 A | 5/1981 | Robertson, Jr. et al. | |
| 4,494,553 A | 1/1985 | Sciarra et al. | |
| 5,002,060 A | 3/1991 | Nedivi | |
| 5,549,113 A | 8/1996 | Halleck et al. | |
| 5,738,102 A | 4/1998 | Lemelson | |
| 5,825,293 A | 10/1998 | Ahmed et al. | |
| 5,906,004 A | 5/1999 | Lebby et al. | |
| 6,015,388 A | 1/2000 | Sackner et al. | |
| 6,047,203 A | 4/2000 | Sackner et al. | |
| 6,080,690 A | 6/2000 | Lebby et al. | |
| 6,198,394 B1 | 3/2001 | Jacobsen et al. | |
| 6,268,725 B1 | 7/2001 | Vernon et al. | |
| 6,341,504 B1 | 1/2002 | Istook | |
| 6,450,957 B1 | 9/2002 | Yoshimi et al. | |
| 6,454,719 B1 | 9/2002 | Greenhut | |
| 6,468,234 B1 | 10/2002 | Van der Loos et al. | |
| 6,517,497 B2 | 2/2003 | Rymut et al. | |
| 6,527,729 B1 | 3/2003 | Turcott | |
| 6,551,252 B2 | 4/2003 | Sackner et al. | |
| 6,599,251 B2 | 7/2003 | Chen et al. | |
| 6,600,949 B1 | 7/2003 | Turcott | |
| 6,727,197 B1 | 4/2004 | Wilson et al. | |
| 6,790,183 B2 | 9/2004 | Murphy | |
| 6,840,907 B1 | 1/2005 | Brydon | |
| 6,858,006 B2 | 2/2005 | MacCarter et al. | |
| 7,267,262 B1 | 9/2007 | Brown | |
| 7,267,652 B2 | 9/2007 | Coyle et al. | |
| 7,295,928 B2 | 11/2007 | Hassan et al. | |
| 8,083,674 B2 * | 12/2011 | Such et al. | 600/300 |
| 2002/0123701 A1 | 9/2002 | Eriksen et al. | |
| 2004/0117204 A1 | 6/2004 | Mazar et al. | |
| 2004/0122334 A1 | 6/2004 | Yamashiro | |
| 2004/0133079 A1 | 7/2004 | Mazar et al. | |
| 2005/0054941 A1 | 3/2005 | Ting | |
| 2006/0122528 A1 * | 6/2006 | Gal | 600/534 |
| 2007/0011919 A1 * | 1/2007 | Case, Jr. | 36/132 |
| 2007/0169364 A1 | 7/2007 | Townsend et al. | |
| 2007/0208235 A1 * | 9/2007 | Besson et al. | 600/301 |
| 2008/0039700 A1 | 2/2008 | Drinan et al. | |
| 2008/0045815 A1 | 2/2008 | Derchak et al. | |
| 2008/0082018 A1 | 4/2008 | Sackner et al. | |
| 2008/0223131 A1 | 9/2008 | Vannucci et al. | |
| 2008/0269644 A1 | 10/2008 | Ray | |
| 2009/0047645 A1 | 2/2009 | DiBenedetto et al. | |
| 2009/0088608 A1 * | 4/2009 | Mumford et al. | 600/300 |
| 2009/0149736 A1 * | 6/2009 | Skidmore et al. | 600/421 |
| 2010/0022861 A1 * | 1/2010 | Cinbis et al. | 600/325 |
| 2010/0027515 A1 | 2/2010 | Hylton | |
| 2010/0037489 A1 * | 2/2010 | Berner et al. | 36/136 |
| 2010/0063779 A1 * | 3/2010 | Schrock et al. | 702/188 |
| 2010/0249541 A1 * | 9/2010 | Geva et al. | 600/301 |
| 2010/0292050 A1 | 11/2010 | DiBenedetto et al. | |
| 2011/0009766 A1 | 1/2011 | McCool | |
| 2011/0153701 A1 | 6/2011 | Moudgill | |
| 2011/0255454 A1 | 10/2011 | Hauser et al. | |
| 2012/0028762 A1 | 2/2012 | Oleson et al. | |
| 2012/0309300 A1 * | 12/2012 | Howard et al. | 455/39 |

FOREIGN PATENT DOCUMENTS

| | | |
|---|---|---|
| WO | WO 2006/009830 A2 | 1/2006 |
| WO | WO 2007/069111 A2 | 6/2007 |
| WO | WO 2009/074973 A1 | 6/2009 |

OTHER PUBLICATIONS

DeCarlo, et al., "Integrating Anatomy and Physiology for Behavior Modeling", Medicine Meets Virtual Reality 3 (San Diego, 1995).

McCool, et al., "Estimates of Ventilation From Body Surface Measurements in Unrestrained Subjects", J. Appl. Physiol., vol. 61, pp. 1114-1119 (1986).

Mead, et al., "Pulmonary Ventilation Measured from Body Surface Movements", Science, pp. 196, 1383-1384 (1967).

Paek, et al., "Postural Effects on Measurements of Tidal Volume From Body Surface Displacements", J. Appl. Physiol., vol. 68, pp. 2482-2487 (1990).

Smith, et al., "Three Degree of Freedom Description of Movement of the Human Chest Wall", J. Appl. Physiol., vol. 60, pp. 927-934 (1986).

Wade, O.L., "Movements of the Thoracic Cage and Diaphragm in Respiration", J. Physiol., pp. 124-193 (1954)

Co-pending U.S. Appl. No. 12/869,578, inventors Derchak et al., filed Aug. 26, 2010.

Co-pending U.S. Appl. No. 12/869,582, inventors Derchak et al., filed Aug. 26, 2010.

Co-pending U.S. Appl. No. 12/869,576, inventor Stone, Robert, filed Aug. 26, 2010.

Co-pending U.S. Appl. No. 12/869,585, inventor Derchak, P. Alexander, filed Aug. 26, 2010.

Co-pending U.S. Appl. No. 12/872,174, inventor Derchak et al., filed Aug. 31, 2010.

Co-pending U.S. Appl. NO. 12/869,625, inventor Derchak, P. Alexander, filed Aug. 26, 2010.

Co-pending U.S. Appl. No. 12/869,586, inventor Derchak et al., filed Aug. 26, 2010.

Co-pending U.S. Appl. No. 12/836,421, inventors Powch, et al., filed Jul. 14, 2010.

* cited by examiner

MULTIMODAL METHOD AND SYSTEM FOR TRANSMITTING INFORMATION ABOUT A SUBJECT

CROSS-REFERENCE TO RELATED APPLICATIONS

This non-provisional application claims priority to U.S. Provisional Application No. 61/275,587, filed on Sep. 1, 2009, which is incorporated herein by reference in its entirety.

FIELD OF THE INVENTION

The present invention relates generally to methods and systems for monitoring characteristics of a subject, including physiological characteristics, performance characteristics, respiratory characteristics, spatial characteristics, and contextual information. More particularly, the invention relates to a multimodal method and system to transmit physiological and athletic performance characteristics, spatial parameters, respiratory characteristics, and contextual information, in real-time. The methods and systems of the present invention can be applied in a variety of fields (e.g., health care, medical diagnosis and monitoring, and athletic monitoring and coaching).

BACKGROUND OF THE INVENTION

In medical diagnosis and treatment of a subject, and in athletic monitoring of a subject, it is often necessary to assess one or more physiological or performance characteristics or symptoms associated with the subject. Athletic performance and progress are often evaluated by examining changes in physiological and/or performance characteristics. Respiratory air volume and other respiratory characteristics can be useful to assess athletic performance, for example, by aiding in detection of changes in physiological state and/or performance characteristics. A key respiratory characteristic is respiratory air volume (or tidal volume).

Monitoring physiological and performance parameters of a subject can be important in planning and evaluating athletic training and activity. A subject may exercise or otherwise engage in athletic activity for a variety of reasons, including, for example, to maintain or achieve a level of fitness, to prepare for or engage in competition, and for enjoyment. The subject may have a training program tailored to his or her fitness level and designed to help him or her progress toward a fitness or exercise goal. Physiological and performance parameters of a subject can provide useful information about the subject's progression in a training program, or about the athletic performance of the subject. In order to accurately appraise the subject's fitness level or progress toward a goal, it may be useful to determine, monitor, and record various physiological or performance parameters, and related contextual information.

Various methods and systems utilizing heart rate have been introduced to approximate effort and physiological stress during exercise. Convenient, practicable, and comfortable means of measuring pulmonary ventilation in non-laboratory conditions, however, have been scarce. While of good value, heart rate can only give an approximation as to the true physiological state of an athlete or medical patient, as it can be confounded by external factors including, for example, sleep levels, caffeine, depressants, beta blockers, stress levels, hydration status, temperature, etc. Furthermore, accurate use of heart rate to gauge physiological performance requires knowledge of the amount of blood flowing to the muscles, which in turn requires knowledge of the instantaneous stroke volume of the heart as well as the rate of pumping. These parameters can be difficult to determine while a subject is engaging in a physical activity.

In addition, chronic diseases are often expressed by episodic worsening of clinical symptoms. Preventive treatment of chronic diseases may reduce the overall dosage of required medication and associated side effects, and may lower mortality and morbidity. Generally, preventive treatment should be initiated or intensified as soon as the earliest clinical symptoms are detected, in order to prevent progression and worsening of the clinical episode and to stop and reverse the pathophysiological process.

Many chronic diseases cause systemic changes in vital signs, such as, for example, breathing and heartbeat patterns, through a variety of physiological mechanisms. For example, common respiratory disorders, such as asthma, chronic obstructive pulmonary disease (COPD), and cystic fibrosis (CF), are direct modifiers of breathing and/or heartbeat patterns. Other chronic diseases, such as diabetes, epilepsy, and certain heart conditions (e.g., congestive heart failure (CHF)), are also known to modify cardiac and breathing activity. In the case of certain heart conditions, such modifications typically occur because of pathophysiologies related to fluid retention and general cardiovascular insufficiency. Other signs, such as coughing and sleep restlessness, are also known to be of importance in some clinical situations.

Many chronic diseases induce systemic effects on vital signs. For example, some chronic diseases interfere with normal breathing and cardiac processes during wakefulness and sleep, causing abnormal breathing and heartbeat patterns.

Breathing and heartbeat patterns may be modified via various direct and indirect physiological mechanisms, resulting in abnormal patterns related to the cause of modification. Some respiratory diseases (e.g., asthma) and some heart conditions (e.g., CHF) are direct breathing modifiers. Other metabolic abnormalities (e.g., hypoglycemia and other neurological pathologies affecting autonomic nervous system activity) are indirect breathing modifiers.

Asthma is a chronic disease with no known cure. Substantial alleviation of asthma symptoms is, however, possible via preventive therapy, such as the use of bronchodilators and anti-inflammatory agents. Asthma management presents a serious challenge to the patient and physician as preventive therapies may require constant monitoring of lung function and corresponding adaptation of medication type and dosage.

Asthma episodes usually develop over a period of several days, although they may sometimes seem to appear unexpectedly. The gradual onset of the asthmatic episode provides an opportunity to start countermeasures to stop and reverse the inflammatory process. Early treatment at the pre-episode stage may reduce the clinical episode manifestation considerably, and may even prevent the transition from the pre-clinical stage to a clinical episode altogether.

Two techniques are generally used for asthma monitoring. The first technique, spirometry, evaluates lung function using a spirometer (i.e., an instrument that measures the volume of air inhaled and exhaled by the lungs). Airflow dynamics are measured during a forceful, coordinated inhalation and exhalation effort by the patient into a mouthpiece connected via a tube to the spirometer. A peak-flow meter is a simpler device that is similar to the spirometer, and is used in a similar manner.

The second technique evaluates lung function by measuring nitric-oxide concentration using a dedicated nitric-oxide monitor. The patient breathes into a mouthpiece connected via a tube to the monitor.

Efficient asthma management may require daily monitoring of respiratory function, which is generally impractical, particularly in non-clinical or home environments. Peak-flow meters and nitric-oxide monitors provide a general indication of the status of lung function; however, these monitoring devices do not possess predictive value, and are used as during-episode markers. In addition, peak-flow meters and nitric-oxide monitors require active participation of the patient, which is difficult to obtain from many children and substantially impossible to obtain from infants.

CHF is a condition in which the heart is weakened and unable to circulate blood to meet the body's needs. The subsequent buildup of fluids in the legs, kidneys, and lungs characterizes the condition as congestive. The weakening may be associated with either the left, right, or both sides of the heart, with different etiologies and treatments associated with each type. In most cases, it is the left side of the heart that fails, so that it is unable to efficiently pump blood to the systemic circulation. The ensuing fluid congestion of the lungs results in changes in respiration, including alterations in rate and/or pattern, accompanied by increased difficulty in breathing and tachypnea.

Quantification of such abnormal breathing provides a basis for assessing CHF progression. For example, Cheyne-Stokes Respiration (CSR) is a breathing pattern characterized by rhythmic oscillation of tidal volume with regularly recurring periods of alternating apnea and hyperapnea. While CSR may be observed in a number of different pathologies (e.g., encephalitis, cerebral circulatory disturbances, and lesions of the bulbar center of respiration), it has also been recognized as an independent risk factor for worsening heart failure and reduced survival in patients with CHF.

In CHF, CSR is associated with frequent awakening that fragments sleep, and with concomitant sympathetic activation, both of which may worsen CHF. Other abnormal breathing patterns may involve periodic breathing, prolonged expiration or inspiration, or gradual changes in respiration rate usually leading to tachypnea.

Pulsus paradoxus is a physical sign present in a variety of cardiac and extra-cardiac conditions, and is of valuable diagnostic and prognostic significance. Pulsus paradoxus is generally defined as a fall in systolic blood pressure of over 10 mmHg during inspiration. Pulsus paradoxus has been associated with the following conditions: cardiac tamponade, pericardial effusion, constrictive pericarditis, restrictive cardiomyopathy, pulmonary embolism, acute myocardial infarction, cardiogenic shock, bronchial asthma, tension pneumothorax, anaphylactic shock, volvulus of the stomach, diaphragmatic hernia, and superior vena cava obstruction.

In bronchial asthma, pulsus paradoxus is of significance because it has often been associated with mild obstructions and can therefore serve as an early warning sign.

Various systems and methods have thus been developed to obtain and transmit physiological and contextual information associated with a subject to a monitoring station.

U.S. Pat. No. 6,468,234, issued Oct. 22, 2002, describes an apparatus for measuring sleep quality that utilizes sensors incorporated in a sheet that is laid on top of a conventional mattress on which the subject sleeps. The sensors collect information, such as the subject's position, temperature, sound/vibration/movement, and optionally other physical properties.

The apparatus includes one or more layers of arrays of integrated sensors, which can be incorporated in layer pads and then placed on a conventional mattress, one or more controllers coupled with the arrays of integrated sensors in each layer pad for the purpose of acquiring data from the sensors, real-time analysis software for analyzing data acquired by the controller from the array of integrated sensors, interface software for collecting user lifestyle data, lifestyle correlation software for correlating the lifestyle data with the data acquired by the array of sensors, and one or more active components to improve sleep quality based on the data acquired through the sensors and the lifestyle data. The array of sensors provides one or more of the following data: position, temperature, sound, vibration, and movement data.

U.S. Pat. No. 6,840,907, issued Jan. 11, 2005, describes a respiratory analysis system for monitoring a respiratory variable of a patient. The system includes a sensor array for accommodating a patient in contact therewith and a processing means. The array has a plurality of independent like sensors for measuring respiratory movement at different locations on the patient to generate a set of independent respiratory movement signals. The processing means receives and processes the movement signals to derive a classification of individual breaths using, for each breath, the respective phase and/or amplitude of each movement sensor signal within the set for that breath.

U.S. Pat. No. 6,517,497, issued Feb. 11, 2003, describes techniques for monitoring and/or quantitatively measuring a patient's respiration using a flexible piezoelectric film sensor. The apparatus includes a piezoelectric film that converts acoustical waves generated by the patient's respiration into electrical signals. The piezoelectric film sensor can be used to monitor the respiration of a patient by correlating the sound generated in the patient's airway with respiratory activity. The data generated by the sensor may be further analyzed by a patient monitor to diagnose respiratory conditions.

U.S. Pat. No. 5,002,060, issued Mar. 26, 1991, describes a monitoring system adapted to simultaneously monitor cardiac and respiratory rates and characteristics and substantial changes in temperature of a subject. The system uses sensors which are passive and non-invasive, and located remotely from (i.e., completely off of) the subject. Sensor signals are processed in order to provide an alarm accompanied with displayed indication of any irregularities in the cardiac and respiratory rates and characteristics, and substantial changes in temperature.

U.S. Pat. No. 6,450,957, issued Sep. 17, 2002, describes a respiration monitoring system that monitors the state of disorder of the respiratory system of a sleeping patient based on the detection of respiratory body movement, without the need to put sensors directly on the patient's body. The system includes weight sensors that produce weight signals attributable to the patient's respiratory body movement. From weight signals having a frequency band of respiration, a respiratory body movement signal is produced. The fall of blood oxygen saturation, which occurs during obstructive apnea of the sleeping patient, is determined based on the variation pattern of the amplitude of the respiratory body movement signal.

U.S. Pat. No. 6,790,183, issued Sep. 14, 2004, describes a lung sound diagnostic system for use in collecting, organizing, and analyzing lung sounds associated with the inspiration(s) and expiration(s) of a patient. The system includes a plurality of transducers that may be placed at various sites around the patient's chest. The microphones are coupled to signal processing circuitry and A/D converters that digitize the data and preferably provide the digital data to a computer station. The system may also include application programs for detecting and classifying abnormal sounds. Additionally, the system may include an analysis program for comparing selected criteria corresponding to the detected abnormal sounds with predefined thresholds in order to provide a likely diagnosis. Also described are a system and method for differentiating between the crackles produced by a patient with interstitial pulmonary fibrosis (IPF) from the crackles produced by a CHF patient.

U.S. Pat. No. 5,738,102, issued Apr. 14, 1998, describes a system for monitoring and computer analyzing select physiological variables of a patient in real time in order to alert medical personnel to the need for medical treatment or to automatically administer such treatment under computer control. The physiological variables monitored by the system may include lung sounds, respiratory rate and rhythm, heart rate and rhythm, heart sounds, and body temperature. Coded signals relating to the physiological variables are produced and compared with reference versions of same by a decision computer in order to evaluate the patient's condition. If the evaluation indicates medical treatment is needed, the decision computer activates a local and/or a remote alarm to alert medical personnel and/or activates one or more actuators for administering a medical treatment such as the injection or infusion of a drug.

Examples of body sounds that may be detected are respiratory sounds and heart sounds. In the case of the former, the computer produces coded signals representing the rate and rhythm of breathing derived from the respiratory sounds.

The system is described as being able to detect abnormal breathing patterns such as apnea, tachypnea, hyperpnea (e.g., Kussmaul breathing associated with metabolic acidosis), bradypnea, Cheyne-Stokes breathing, ataxic breathing, and obstructive breathing. Coded signals may also be generated from the respiratory sounds that indicate the presence of added lung sounds such as rales associated with pneumonia and pulmonary edema, wheezes associated with obstructive lung disease, and pleural rubs due to inflammation of the pleural membranes.

U.S. Pat. No. 6,599,251, issued Jul. 29, 2003, describes non-invasive techniques for monitoring the blood pressure of a subject. A pulse signal is detected at both a first and second location on the subject's body. The elapsed time between the arrival of corresponding points of the pulse signal at the first and second locations is determined. Blood pressure is related to the elapsed time by mathematical relationships.

U.S. Patent Application Publication No. 2004/0133079, published Jul. 8, 2004, describes techniques for predicting patient health and patient relative well-being within a patient management system. One embodiment utilizes an implantable medical device including an analysis component and a sensing component further including a three-dimensional accelerometer, a transthoracic impedance sensor, a cardioactivity sensor, an oxygen saturation sensor, and a blood glucose sensor. One analysis described is detecting changes in transthoracic impedance variation patterns that are indicative of the early occurrence of a new disease state (such as Chronic Obstructive Pulmonary Disease), the onset of an illness (such as asthma), or the progression of a disease (such as DC impedance indicating lung fluid accumulation that corresponds to the progression of heart failure).

U.S. Pat. No. 6,454,719, issued Sep. 24, 2002, describes techniques for determining the cardiac condition of a patient by a cardiac monitor apparatus using a respiration parameter such as a current respiration signal or a respiration rate. The variability of the respiration parameter is used to generate a signal indicative of the current heart failure status of the patient, and, more particularly, whether the patient's condition has improved, worsened, or remained unchanged over a predetermined time period. The circuitry for detecting the respiration parameter may be implanted in the patient, for example as part of a pacemaker, while at least some of the analyzing circuitry may be external and remote from the patient. Alternatively the whole device may be implantable.

U.S. Pat. No. 6,600,949, issued Jul. 29, 2003, describes a method for monitoring the condition of a heart failure patient using respiration patterns. An implantable or other ambulatory monitor senses the patient's respiratory patterns to identify the presence of periodic breathing or Cheyne-Stokes respiration. In a first embodiment, mechanical changes of the thorax due to breathing are detected and this data is used to recognize hyperventilation and apnea or hypoventilation. In a second embodiment, Cheyne-Stokes respiration is recognized by detecting changes in blood or tissue pH or $CO_2$ concentration and partial pressure. In another embodiment, changes in pulse amplitude associated with Cheyne-Stokes respiration are detected. Alternating loss and return of respiration-induced amplitude modulation or pulse-interval variation may also be used to identify the presence of Cheyne-Stokes respiration.

In yet another embodiment, modulation of the average heart rate over time is monitored and its absence is used as an indicator of Cheyne-Stokes respiration. This information may be used to warn the patient or healthcare provider of changes in the patient's condition warranting attention.

U.S. Pat. No. 6,527,729, issued Mar. 4, 2003, describes a method for monitoring the disease progression of a heart failure patient. An implantable or other ambulatory monitor senses acoustic signals, including heart and lung sounds within the patient. Significant changes in the energy content of either the heart or lung sounds is indicative of a heart failure exacerbation.

U.S. Pat. No. 6,015,388, issued Jan. 18, 2000, to Sackner et al. (VivoMetrics, Inc.) describes a method for measuring respiratory drive, including determining a peak inspiratory flow and a peak inspiratory acceleration from a breath waveform derived from rib cage motion and abdominal motion using a plethysmograph or other external respiratory measuring device. The respiratory drive is ascertainable even during complete blockage of the respiratory system. In one embodiment, the peak inspiratory drive is used to initiate inspiration in a mechanical ventilator and for determining an index describing a shape of the waveform for controlling a continuous positive air pressure (CPAP) device.

U.S. Pat. No. 6,047,203, issued Apr. 4, 2000, to Sackner et al. (VivoMetrics, Inc.) describes physiological monitoring apparel worn by a monitored individual, the apparel having attached sensors for monitoring parameters reflecting pulmonary function, cardiac function, or the function of other organ systems. In one embodiment, an alarm is generated based on a trend progressing over one to a few hours.

There are several drawbacks associated with the noted prior art systems and methods. A major drawback is that prior art systems and associated methods have limited means for transmitting signals acquired from a medical patient or athlete to a monitoring station.

BRIEF SUMMARY OF THE INVENTION

The present invention provides apparatuses and methods for monitoring a medical patient or athlete and transmitting information about the patient or athlete. For example, the present invention provides a system for transmitting information about a subject engaged in a physical activity, the system including a data acquisition subsystem configured to generate a first signal and a second signal, each representing a physiological characteristic of the subject, a performance characteristic of the subject, a respiratory characteristic of the subject, or a spatial characteristic of the subject, and a data transmission subsystem configured to transmit the first signal and the second signal from the data acquisition subsystem to a monitoring subsystem, wherein the first signal is transmitted using a first transmission mode, and wherein the second signal is transmitted using a second transmission mode, the second transmission mode being different from the first transmission mode.

The system can also be configured to transmit signals related to various characteristics associated with physical activity of the subject. The system may include or transmit signals from or to one or more sensors for detecting information used to measure and/or calculate performance parameters. Suitable sensors may include, for example, the sensors disclosed in commonly owned U.S. patent application Ser. No. 11/892,023, filed Feb. 19, 2009, titled "Sports Electronic Training System, and Applications Thereof," commonly owned U.S. patent application Ser. No. 12/467,944, filed May 18, 2009, titled "Portable Fitness Monitoring Systems, and Applications Thereof," and commonly owned U.S. patent application Ser. No. 12/836,421, filed Jul. 14, 2010, titled "Fitness Monitoring Methods, Systems, and Program Products, and Applications Thereof," each of which is incorporated herein by reference in its entirety.

The present invention also provides a method for transmitting information about a subject, e.g., an athlete or medical patient, the method including generating a first signal and a second signal, each representing a physiological characteristic of a subject, a performance characteristic of a subject, a respiratory characteristic of a subject, or a spatial characteristic of a subject, and transmitting the first signal and the second signal to a monitoring subsystem, wherein the first signal is transmitted using a first transmission mode, and wherein the second signal is transmitted using a second transmission mode, the second transmission mode being different from the first transmission mode.

The present invention provides multimodal communications systems for transmitting signals representing physiological, performance, and contextual information associated with a subject. An embodiment of the present invention also provides multimodal communications means including multiple radio subsystems (or modes) that enable connection to an external monitoring device to be acquired in a wide range of settings where a single radio mode would be ineffective. Additionally, combining the multimodal communications means of the invention with real-time data-processing allows the communications functionality to be engaged only when data determined to be relevant to the user is identified.

BRIEF DESCRIPTION OF THE FIGURES

Further features and advantages will become apparent from the following and more particular description of the present invention, as illustrated in the accompanying drawings, in which like referenced characters generally refer to the same parts or elements throughout the views.

DETAILED DESCRIPTION OF THE INVENTION

Figure 1:
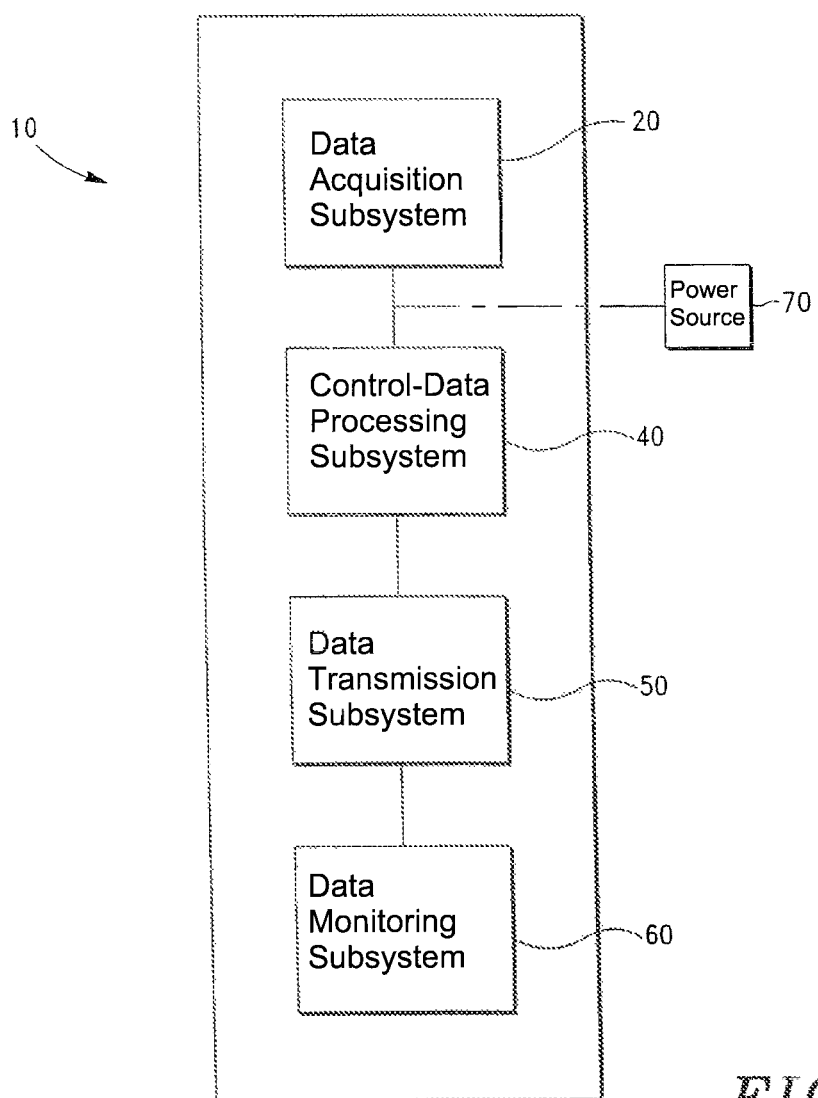
FIG. 1 is a schematic illustration of a physiology monitoring system, according to one embodiment of the invention.

Before describing the present invention in detail, it is to be understood that this invention is not limited to particularly exemplified methods, apparatuses, systems or circuits, as such may, of course, vary. Thus, although a number of methods and systems similar or equivalent to those described herein can be used in the practice of the present invention, exemplary embodiments are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

As used in this specification and the appended claims, the singular forms "a", "an", and "the" include plural referents unless the content clearly dictates otherwise.

Further, all publications, patents, and patent applications referenced herein, whether supra or infra, are hereby incorporated by reference in their entirety.

The publications discussed herein are provided solely for their disclosure prior to the filing date of the present application. Nothing herein is to be construed as an admission that the present invention is not entitled to antedate such publication(s) by virtue of prior invention. Further, the dates of publication may be different from the actual publication dates, which may need to be independently confirmed.

DEFINITIONS

The terms "respiratory parameter" and "respiratory characteristic", as used herein, mean and include a characteristic associated with the respiratory system and functioning thereof, including, without limitation, breathing frequency (fB), tidal volume ($V_T$), inspiration volume ($V_I$), expiration volume ($V_E$), minute ventilation (VE), inspiratory breathing time, expiratory breathing time, and flow rates (e.g., rates of change in the chest wall volume). The terms "respiratory parameter" and "respiratory characteristic" further mean and include inferences regarding ventilatory mechanics from synchronous or asynchronous movements of the chest wall compartments.

According to the present invention, flow rates and respiratory accelerations can be determined from a volume signal. Further, numerous inferences regarding ventilatory mechanics can be drawn from the degree of asynchrony in movement occurring among the discrete compartments that make up the chest wall.

The terms "respiratory system disorder", "respiratory disorder", and "adverse respiratory event", as used herein, mean and include any dysfunction of the respiratory system that impedes the normal respiration or ventilation process.

The terms "physiological parameter" and "physiological characteristic", as used herein, mean and include, without limitation, electrical activity of the heart, electrical activity of other muscles, electrical activity of the brain, pulse rate, blood pressure, blood oxygen saturation level, skin temperature, and core temperature.

The terms "spatial parameter" and "spatial characteristic", as used herein, mean and include a subject's orientation and/or movement.

The terms "patient" and "subject", as used herein, mean and include humans and animals.

Pulmonary ventilation, tidal volume, respiratory rate, and other associated respiratory characteristics can provide a reliable and practical measure of oxygen and carbon dioxide transpiration in a living body. Respiratory characteristics are directly connected to exercise effort, physiological stress, and other physiological characteristics. One way to externally determine tidal volume is to measure the change in thoracic volume. Change in thoracic volume is caused by the expansion and contraction of the lungs. As the gas pressure in the lungs at the maxima and minima of the pressure ranges is equilibrated to surrounding air pressure, there is a very close and monotonic relationship between the volume of the lungs and the volume of air inspired.

Accurate measurement of the change in thoracic volume involves measuring the change in the diameter of the chest at the ribcage. Measurement of the change in the diameter of the chest below the ribcage can provide additional accuracy to the measurement. Monitoring changes in the diameter of the chest below the ribcage can account for diaphragm delivered breathing where the contraction and relaxation of the diaphragm muscle causes the organs of the abdomen to be pushed down and outwards, thereby increasing the available volume of the lungs.

Monitoring and analyzing respiratory characteristics can be particularly useful in athletic applications, as there is a direct link between performance and an athlete's processing of oxygen and carbon dioxide. For example, in many athletic training situations, it is helpful to know when the athlete's body transitions between aerobic exercise and anaerobic exercise, sometimes referred to as the athlete's ventilatory threshold. Crossing over the ventilatory threshold level is an indicator of pending performance limitations during sport activities. For example, it can be beneficial for athletes to train in the anaerobic state for limited periods of time. However, for many sports, proper training requires only limited periods of anaerobic exercise interrupted by lower intensity aerobic exercises. It is difficult for an athlete to determine which state, anaerobic or aerobic, he or she is in without referencing physiological characteristics such as respiratory characteristics. Therefore, respiratory monitoring and data processing can provide substantial benefits in athletic training by allowing for accurate and substantially instantaneous measurements of the athlete's exercise state. Changes in an athlete's ventilatory threshold over time, as well as patterns of tidal volume during post-exercise recovery, can be valuable to measure improvements in the athlete's fitness level over the course of a training regime. Respiratory monitoring can further allow for monitoring and analyzing changes in a subject's resting metabolic rate.

A second ventilatory threshold exists at the point when the load on the body is such that the pulmonary ventilation is no longer sufficient to support life sustainably. Dwelling too long in this state will lead to collapse and so determination of this point can be of value in medical applications, and particularly to first responders and other emergency response personnel.

As indicated above, the present invention is directed to multimodal methods and systems for transmitting signals representing physiological and contextual information associated with a subject. The present invention utilizes multiple radio modes enabling a connection to be acquired in a wide range of settings where a single radio mode would be ineffective. Additionally, combining multiple radio modes with real-time data-processing allows the communications functionality to be engaged only when data relevant to the user is identified.

Several embodiments of physiology monitoring systems and associated methods having multimodal communication means associated therewith are described in detail below. It is, however, to be understood that the present invention is not limited to the systems and associated methods described herein. According to the invention, the multimodal communications means of the invention can be employed with various physiological monitoring systems and methods.

Referring first to FIG. 1, there is shown a schematic illustration of one embodiment of a physiology monitoring system according to the present invention. As illustrated in FIG. 1, the physiology monitoring system 10 preferably includes a data acquisition subsystem 20, a control-data processing subsystem 40, a data transmission subsystem 50, a data monitoring subsystem 60, and a power source 70, such as a battery. Control-data processing subsystem 40 is also referred to herein as "processor subsystem," "processing subsystem," and "data processing subsystem." The terms control-data processing subsystem, processor subsystem, processing subsystem, and data processing subsystem are used interchangeably in the present application.

Data Acquisition Subsystem

In accordance with one embodiment of the invention, the data acquisition subsystem 20 includes means for acquiring anatomical parameters that can be employed to determine at least one respiratory characteristic, more preferably a plurality of respiratory characteristics, in cooperation with control-data processing subsystem 40, and, in some embodiments, data monitoring subsystem 60. The anatomical parameters may include changes in (or displacements of) the anteroposterior diameters of the rib cage and abdomen, and axial displacement of the chest wall. The means for acquiring the noted parameters, e.g., sensors. The sensors can include paired electromagnetic coils or magnetometers.

Although the present invention is described herein in terms of magnetometers and magnetometer systems, it is understood that other types of sensor systems capable of measuring changes in distance between two or more sensors in the system can be used in place of, or in addition to, magnetometers. Specifically, the invention is not limited to the use of electromagnetic coils or magnetometers to acquire signals representing measured changes in the anteroposterior diameters of the rib cage and abdomen, and axial displacement of the chest wall. Various additional means and devices that can be readily adapted to measure the noted anatomical parameters can be employed within the scope of the invention. Such means and devices include, without limitation, Hall effect sensors and electronic compass sensors. Wireless sensors with the capability of measuring time delay in a signal sent from one sensor to another and thereby determine the distance between the two sensors can be substituted for or provided in addition to magnetometers in accordance with the present invention.

Magnetometers (or other sensors) can be embedded in or carried by a wearable garment, such as a shirt or vest. The wearable monitoring garment eliminates the need to attach the magnetometers directly to the skin of a subject and, hence, resolves all issues related thereto. The wearable monitoring garment also facilitates repeated and convenient positioning of magnetometers at virtually any appropriate (or desired) position on a subject's torso.

According to the invention, at least one, and preferably two, magnetometers are employed to measure the noted subject parameters (or displacements). In some embodiments of the invention, two pairs of magnetometers are thus employed. In some embodiments, more than two pairs of magnetometers are employed.

Figure 2:
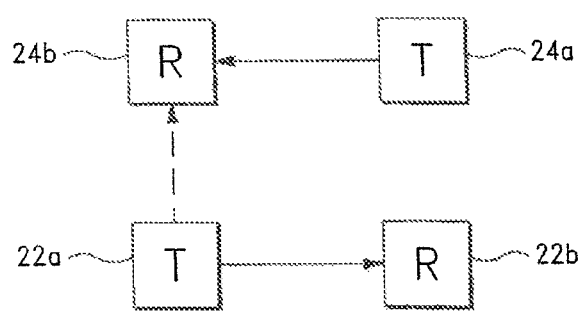
FIG. 2 is a schematic illustration of a dual-paired electromagnetic coil arrangement, according to one embodiment of the invention.

Referring now to FIG. 2, there is shown one embodiment of a dual-paired electromagnetic coil arrangement for detecting and measuring displacement(s) of the rib cage, abdomen, and chest wall. As illustrated in FIG. 2, the electromagnetic coils include first transmission coil 22a, first receive coil 22b, second transmission coil 24a, and second receive coil 24b. In FIG. 2, the letter T designates the transmission coils and the letter R designates the receiving coils, however, the coils are not limited to such designations. The electromagnetic coils of embodiments of the present invention are described as "receiving" or "transmitting," however, each receiving coil can alternatively and independently be a transmitting coil, and each transmitting coil can alternatively and independently be a transmitting coil. Coils can also perform both receiving and transmitting functions.

Details of the noted arrangement and associated embodiments (discussed below) are set forth in co-pending U.S. patent application Ser. No. 12/231,692, filed Sep. 5, 2008, co-pending U.S. Patent Application No. 61/275,576, filed Sep. 1, 2009, and co-pending U.S. patent application Ser. No. 12/869,576, filed Aug. 26, 2010 all of which are expressly incorporated by reference herein in their entirety.

As set forth in the noted applications, in some embodiments, at least receive coil 24b is adapted to receive coil transmissions from each of transmission coils 22a, 24a (i.e., at least receive coil 24b may be a dual function coil, where a "dual function coil" refers to a coil capable of receiving transmissions from a plurality of different transmission coils). In some embodiments, each receive coil 22b, 24b is adapted to receive transmissions from each transmission coil 22a, 24a.

Figure 3:
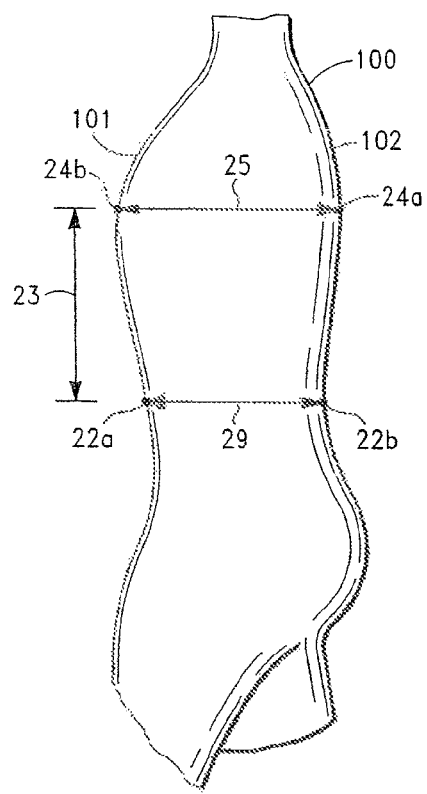
FIG. 3 is a side view of a subject, showing the position of the dual-paired electromagnetic coil arrangement of FIG. 2 on the subject, according to one embodiment of the invention.
Figure 4:
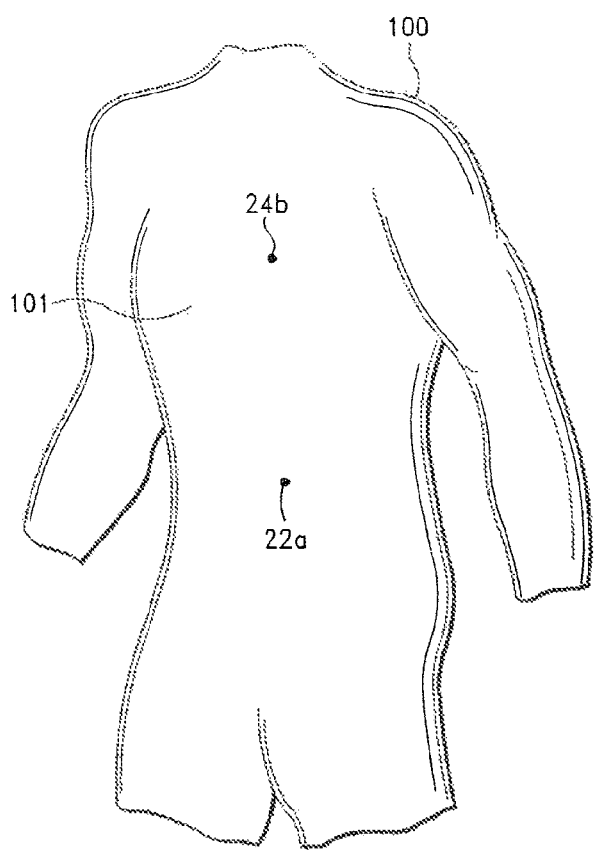
FIG. 4 is a perspective view of the subject, showing the position of electromagnetic coils on the front of the subject, according to one embodiment of the invention.
Figure 5:
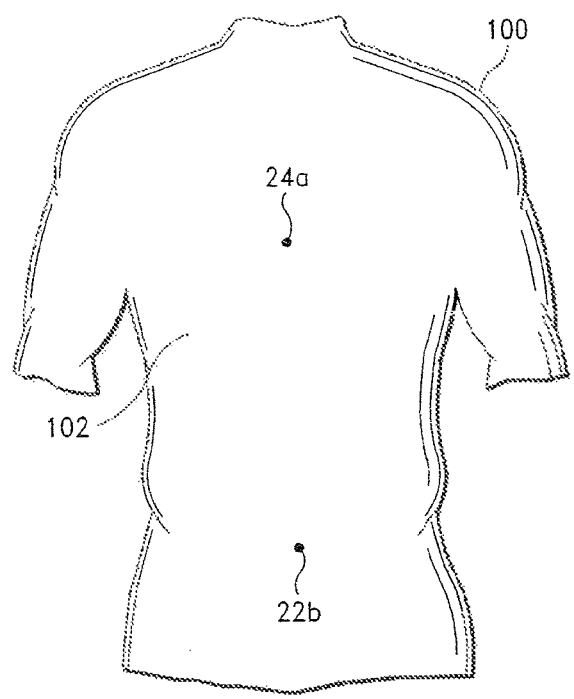
FIG. 5 is a plane view of the subject's back, showing the position of electromagnetic coils thereon, according to one embodiment of the invention.

Referring now to FIGS. 3-5, there are shown coils 22a, 22b, 24a, 24b positioned on a subject or patient 100. As illustrated in FIGS. 3-5, first transmission coil 22a is preferably positioned on front 101 of subject 100 proximate the umbilicus of subject 100, and first receive coil 22b is preferably positioned proximate the same axial position, but on back 102 of subject 100. Second receive coil 24b is preferably positioned on front 101 of subject 100 proximate the base of the sternum and second transmission coil 24a is preferably positioned proximate the same axial position, but on the back 102 of subject 100.

As set forth in co-pending U.S. patent application Ser. No. 12/231,692, the positions of transmission coils 22a, 24a and receive coils 22b, 24b can be reversed (i.e., transmission coil 22a and receive coil 24b can be placed on back 102 of subject 100 and transmission coil 24a and receive coil 22b can be placed on front 101 of subject 100). Both transmission coils 22a and 24a can also be placed on front 101 or back 102 of subject 100, and receive coils 22b and 24b can be placed on the opposite side.

Referring back to FIG. 3, an arrow 23 represents the chest wall or, in this instance, the xiphi-umbilical distance (Xi) that is monitored. An arrow 25 represents the monitored rib cage distance, while an arrow 29 represents the monitored abdominal distance.

In one embodiment, wherein coil 24b is a dual function coil, as subject or patient 100 breathes, displacement(s) of the rib cage and abdomen (i.e., changes in the distance between each pair of coils 22a, 22b and 24a, 24b, denoted, respectively, by arrow 29 and arrow 25) is determined from measured changes in voltage between paired coils 22a, 22b and 24a, 24b. The axial displacement of the chest wall, denoted by arrow 23 (e.g., xiphiumbilical distance (Xi)) is also determined from measured changes in voltage between transmission coil 22a and receive coil 24b.

As indicated above, more than two pairs of electromagnetic coils can be employed to acquire anatomical parameters. As set forth in U.S. Patent Application No. 61/275,575, filed Sep. 1, 2009, and co-pending U.S. patent application Ser. No. 12/869,582, filed Aug. 26, 2010, both of which are expressly incorporated by reference herein in their entirety, adding additional electromagnetic coils in anatomically appropriate positions on a subject provides numerous significant advantages over dual-paired coil embodiments. Among the advantages is the provision of additional (and pertinent) data and/or information regarding chest wall movement(s) and the relationship(s) thereof to respiratory activity and respiratory associated events, such as speaking, sneezing, laughing, and coughing.

Further, the multiple single, cross, and interaction axes of the electromagnetic coil transmissions that result from the additional coils (and placement thereof) provide highly accurate quantification of changes in chest wall volume, and facilitate three-dimensional modeling of chest wall shape and movement of ambulatory subjects, and the evaluation and quantification of ventilatory mechanics (e.g., synchronous and asynchronous movement of the chest wall compartments).

Referring now to FIGS. 6-17, several multiple-paired electromagnetic coil arrangements will now be described in detail. It is, however, to be understood that the invention is not limited to the multiple-paired coil embodiments described herein. Indeed, the multiple-paired coil embodiments can comprise any number of additional pairs of electromagnetic coils (e.g., 3, 4, 5, 6, 7, 8, 9, 10, etc.). For example, in embodiments using three magnetometers, for example, electromagnetic coils, it is understood that the three electromagnetic coils can function as multiple pairs. Specifically, referring to the coils as first, second, and third coils, the first coil can form a pair with the second coil and the first coil can also form a pair with the third coil. In addition, the second coil can also form a pair with the third coil. Thus, a magnetometer system utilizing three electromagnetic coils can be configured to form one, two, or three pairs. Each of the first, second, and third coils can be configured to transmit signals, receive signals, or to both receive and transmit signals. A magnetometer can communicate with a plurality of other magnetometers, and therefore a particular magnetometer can forth a part of more than one pair. The position of the additional coils and the function thereof can also be readily modified and/or adapted for a particular application within the scope of the present invention.

Figure 6:
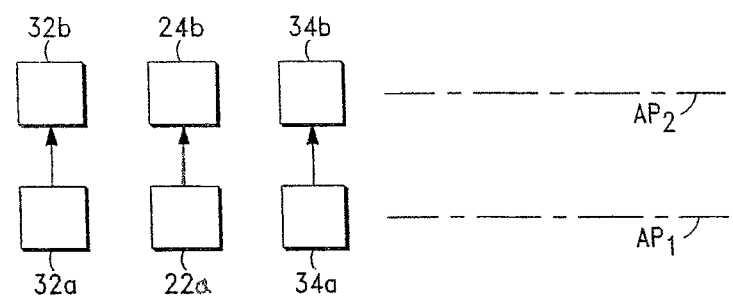
FIGS. 6 and 7 are schematic illustrations of a multiple-paired electromagnetic coil arrangement, according to one embodiment of the invention.
Figure 7:
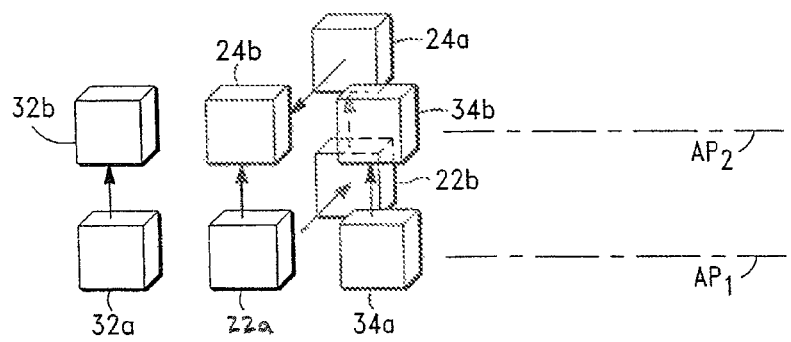
Figure 8:
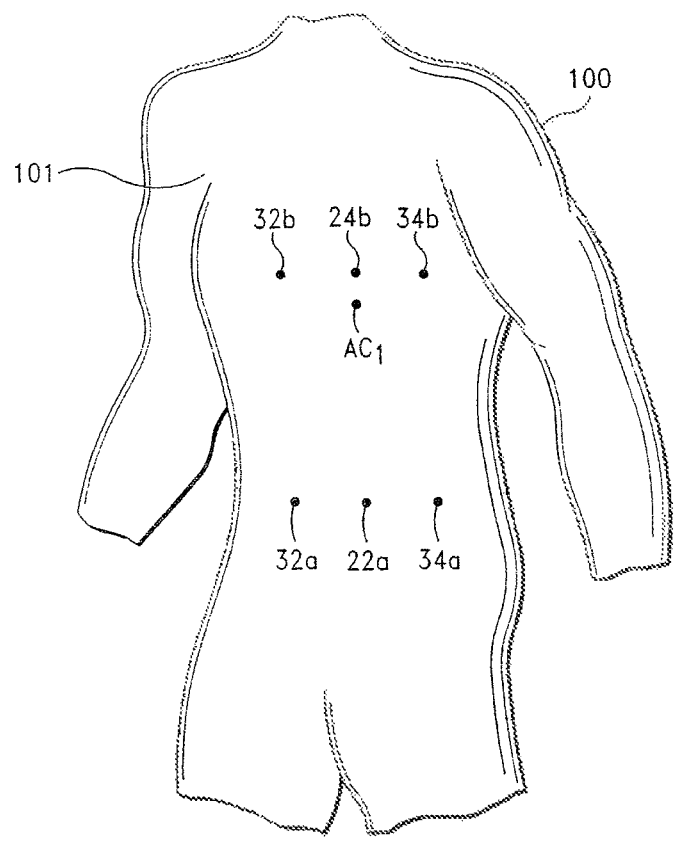
FIG. 8 is a perspective view of a subject, showing the position of the multiple-paired electromagnetic coils shown in FIG. 6 on the front of the subject, according to one embodiment of the invention.

Referring first to FIGS. 6-8, there is shown one embodiment of a multiple-paired coil arrangement. As illustrated in FIG. 7, the noted embodiment similarly includes electromagnetic coils 22a, 22b, 24a, 24b. According to the invention, any of the aforementioned dual-paired coil embodiments associated with coils 22a, 22b, 24a, 24b can be employed with the multiple-paired coil embodiments of the invention.

As also illustrated in FIGS. 6 and 7, the multiple-paired coil arrangement further includes at least two additional pairs of electromagnetic coils: third transmission coil 32a, third receive coil 32b, fourth transmission coil 34a, and fourth receive coil 34b.

In some embodiments, at least one of receive coils 32b, 34b is a dual function coil and, hence, adapted to receive transmissions from each of transmission coils 32a, 22a, 34a. In some embodiments, each receive coil 32b, 34b is adapted to receive transmissions from each transmission coil 32a, 22a, 34a.

Figure 9:
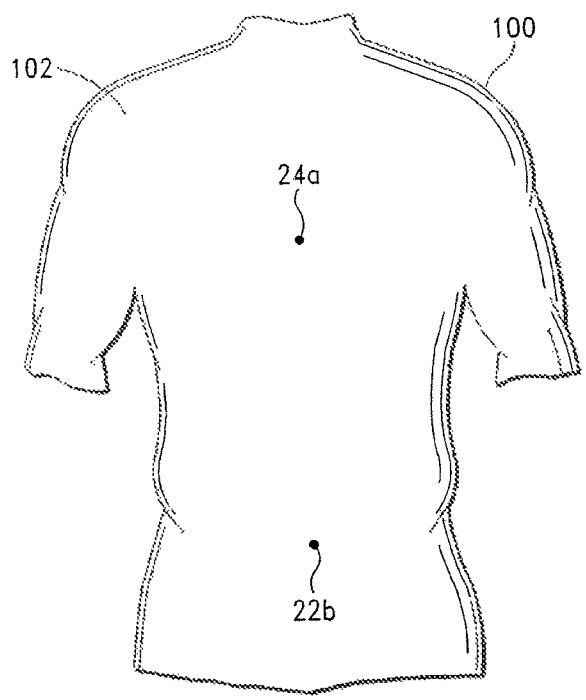
FIG. 9 is a plane view of the subject's back, showing the position of electromagnetic coils thereon, according to one embodiment of the invention.

Referring now to FIGS. 8 and 9, there are shown coils 22a, 22b, 24a, 24b, 32a, 32b, 34a, 34b positioned on a subject or patient 100. As illustrated in FIGS. 8 and 9, first transmission coil 22a is preferably positioned on front 101 of subject 100 proximate the umbilicus of subject 100 and first receive coil 22b is preferably positioned proximate the same axial position, but on back 102 of subject 100. Second receive coil 24b is preferably positioned on front 101 of subject 100 proximate the base of the sternum and second transmission coil 24a is positioned proximate the same axial position, but on back 102 of subject 100.

Third transmission coil 32a is preferably positioned on front 101 of subject 100 and axially spaced to the right of first transmission coil 22a. Fourth transmission coil 34a is preferably positioned on front 101 of subject 100 and axially spaced to the left of first transmission coil 22a. In the illustrated embodiment, each transmission coil 32a, 22a, 34a is preferably positioned proximate the same axial plane (denoted "$AP_1$" in FIGS. 6 and 7).

Third receive coil 32b is preferably positioned on front 101 of subject 100 and axially spaced to the right of second receive coil 24b. Fourth receive coil 34b is preferably positioned on front 101 of subject 100 and axially spaced to the left of second receive coil 24b. Preferably, each receive coil 32b, 24b, 34b is similarly positioned proximate the same axial plane (denoted "$AP_2$" in FIGS. 6 and 7).

The axial spacing of coils 32a, 32b, 34a, 34b will, in many instances, be dependant on the body size and structure of the subject (e.g., adult, female, male, adolescent). The distance between and amongst the coils can also vary with the degree of measurement precision required or desired.

As indicated above, a significant advantage of the multiple-paired coil arrangements is the provision of multiple single, cross, and interaction coil transmission axes that facilitate three-dimensional modeling of chest wall shape and movement of ambulatory subjects, and evaluation and quantification of ventilatory mechanics (e.g., synchronous and asynchronous movement of the chest wall compartments).

A further significant advantage of the multiple-paired coil arrangements is that real-time, three-dimensional models of the chest wall can be created by simultaneous monitoring of the chest wall with the multiple-paired coils.

Figure 10:
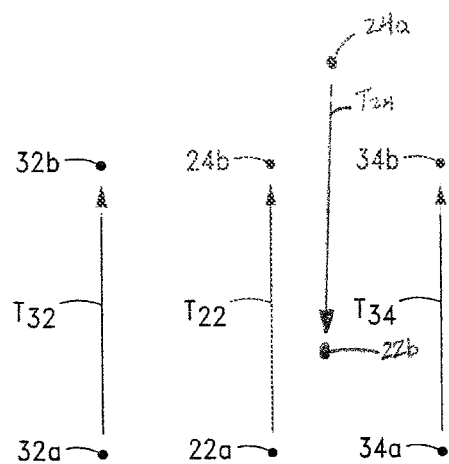
FIG. 10-12 are schematic illustrations of coil transmission axes provided by several multiple-paired coil embodiments of the invention.
Figure 11:
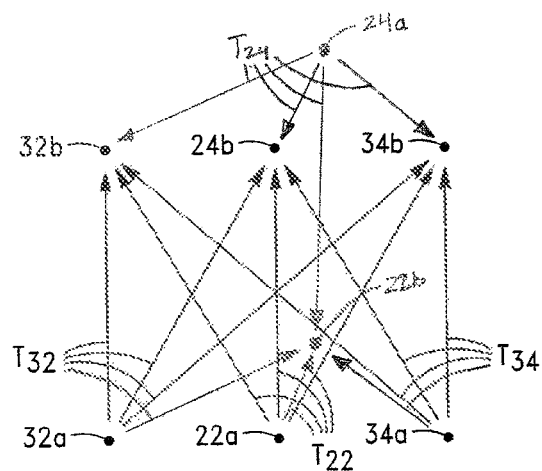
Figure 12:
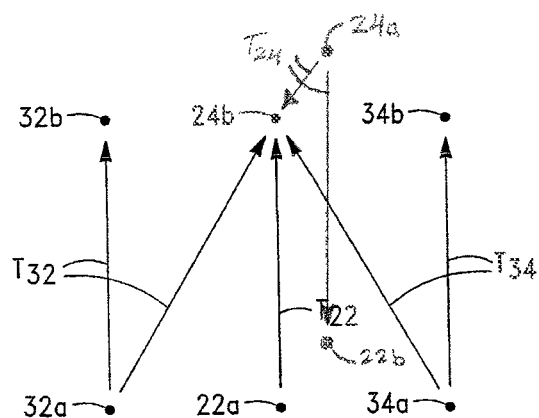

Referring now to FIGS. 10-12, there are shown several schematic illustrations of coil transmission axes provided by three multiple-paired coil embodiments of the invention. Referring first to FIG. 10, there is shown an illustration of coil transmissions, wherein each receive coil 32b, 24b, 34b, 22b is a single function coil. Receive coil 32b is adapted to receive a transmission $T_{32}$ from transmission coil 22a. Receive coil 24b is adapted to receive a transmission $T_{22}$ from transmission coil 22a. Receive coil 34b is adapted to receive a transmission $T_{34}$ from transmission coil 34a. Receive coil 22b is adapted to receive a transmission $T_{24}$ from transmission coil 24a.

Referring now to FIG. 12, there is shown another illustration of coil transmissions, wherein receive coil 24b is a dual function coil. Receive coil 32b is adapted to receive transmission $T_{32}$ from transmission coil 32a, receive coil 34b is adapted to receive transmission $T_{34}$ from transmission coil 34a, and receive coil 22b is adapted to receive transmission $T_{24}$ from transmission coil 24a. Receive coil 24b is, however, adapted to receive transmission $T_{32}$ from transmission coil 32a, transmission $T_{22}$ from transmission coil 22a, transmission $T_{34}$ from transmission coil 34a, and transmission $T_{24}$ from transmission coil 24a.

In FIG. 11, each receive coil 32b, 24b, 34b, 22b is a dual function coil. As illustrated in FIG. 11, receive coil 32b is thus adapted to receive transmission $T_{32}$ from transmission coil 32a, transmission $T_{22}$ from transmission coil 22a, transmission $T_{34}$ from transmission coil 34a, and transmission $T_{24}$ from transmission coil 24a. Receive coils 24b, 34b, and 22b are also adapted to receive transmission $T_{32}$ from transmission coil 32a, transmission $T_{22}$ from transmission coil 22a, transmission $T_{34}$ from transmission coil 34a, and transmission $T_{24}$ from transmission coil 24a.

Figure 13:
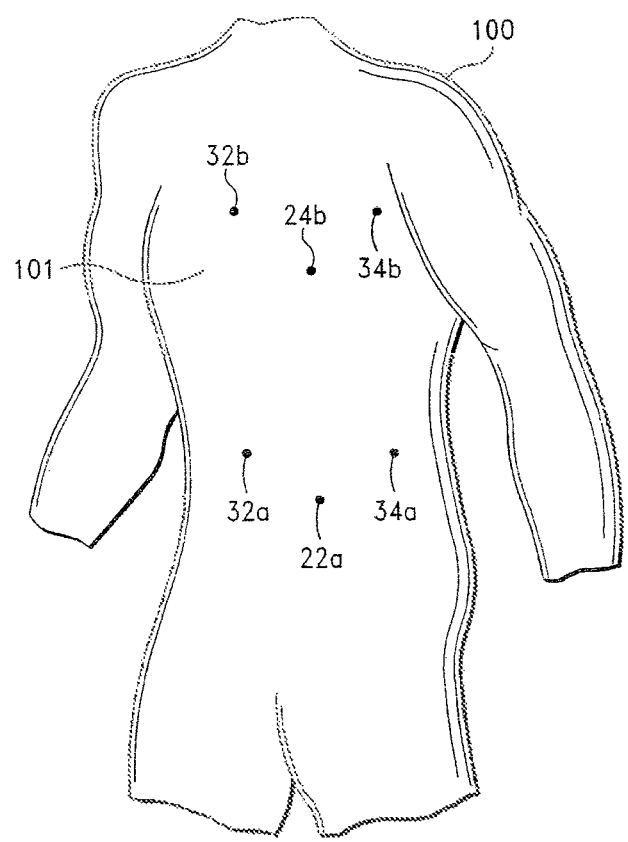
FIG. 13 is a perspective view of a subject, showing alternative positions of the multiple-paired electromagnetic coils shown in FIG. 6 on the front of the subject, according to another embodiment of the invention.

Referring now to FIGS. 13-17, there are shown additional multiple-paired coil arrangements that can be employed within the scope of the present invention. Referring first to FIG. 13, there is shown a multiple-paired coil arrangement, wherein the two additional coil pairs 32a, 32b and 34a, 34b are non-uniformly positioned on front 101 of subject 100. As indicated, the additional coils can be positioned at any appropriate (or desired) positions on the torso of subject 100.

Figure 14:
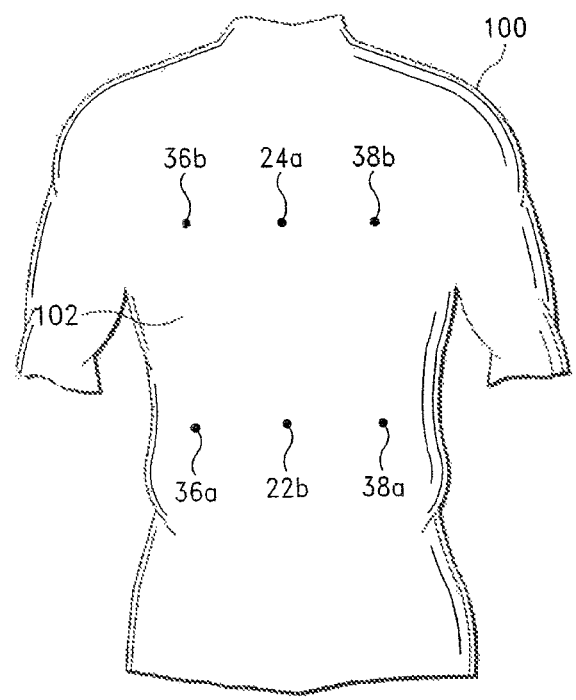
FIG. 14 is a plane view of the subject's back, showing the positioning of three pairs of electromagnetic coils thereon, according to another embodiment of the invention.
Figure 15:
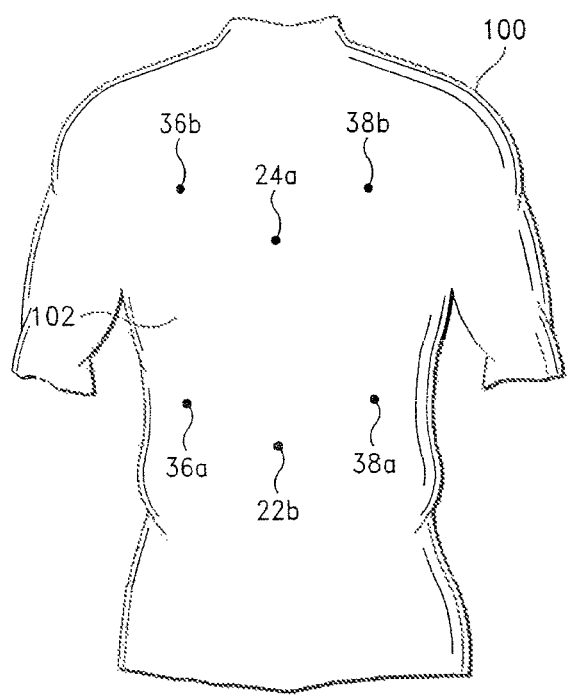
FIG. 15 is a plane view of the subject's back, showing alternative positions of the paired electromagnetic coils shown in FIG. 14 thereon, according to another embodiment of the invention.

Additional coils (e.g., transmission coil 36a paired with receive coil 36b, and transmission coil 38a paired with receive coil 38b) can also be positioned on back 102 of subject 100, as illustrated in FIG. 14. Coils 36a, 36b, 38a, 38b can be positioned uniformly, as shown in FIG. 14, or non-uniformly, as illustrated in FIG. 15.

Figure 16:
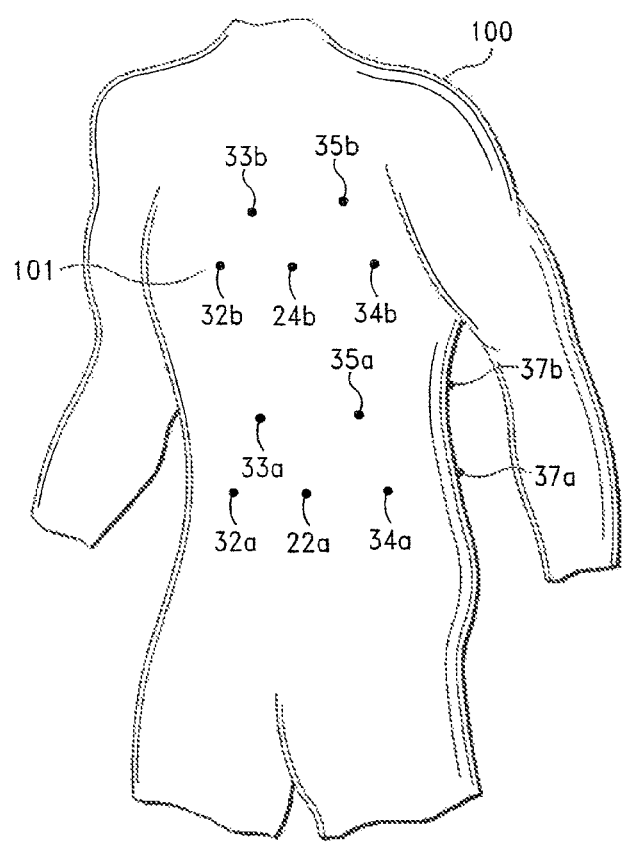
FIG. 16 is a perspective view of a subject, showing the position of six pairs of electromagnetic coils on the front and one side of the subject, according to another embodiment of the invention.
Figure 17:
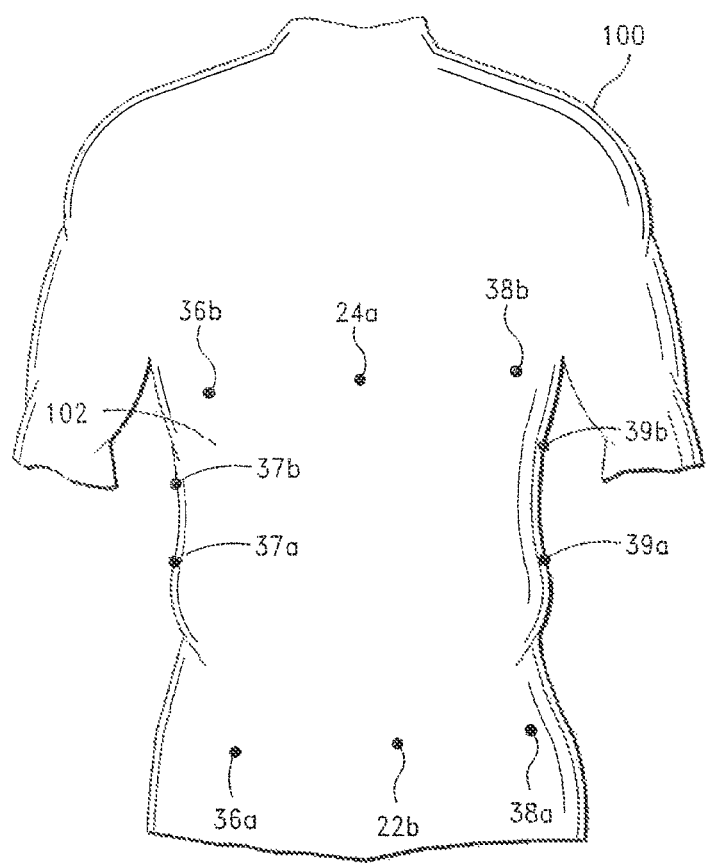
FIG. 17 is a plane view of the subject's back, showing the position of five pairs of electromagnetic coils on the back and both sides of the subject, according to another embodiment of the invention.

Referring now to FIGS. 16-17, there is shown another multiple-paired coil arrangement, wherein additional coils are positioned on the torso of subject 100. As illustrated in FIG. 16, additional coils (e.g., transmission coil 33a paired with receive coil 33b, and transmission coil 35a paired with receive coil 35b) can be positioned on front 101 of subject 100. Additional coils (e.g., transmission coil 37a paired with receive coil 37b, and transmission coil 39a paired with receive coil 39b) can be positioned on opposite sides of subject 100.

Additionally, the transmission coils and receive coils disclosed herein need not necessarily be paired one-to-one. For example, a single receive coil may be configured to receive transmissions from multiple transmission coils, and a single transmission coil may be configured to transmit to multiple receive coils.

Multiple coil embodiments of the invention are not limited to the multiple-paired coil embodiments shown in FIGS.

6-17. It is again emphasized that the multiple-paired coil embodiments can include any number of additional electromagnetic coils. Further, the position of the additional coils and the function thereof can also be readily modified and/or adapted for a particular application within the scope of the present invention.

Data acquisition subsystem 20 can also include means for directly monitoring the orientation and/or movement of subject 100 (e.g., spatial parameters). Such means can include optical encoders, proximity and Hall effect switches, laser interferometry, accelerometers, gyroscopes, and/or global positioning systems (GPS). The data obtained from such means may provide performance parameters or characteristics of a subject engaged in physical activity, such as, for example, speed or acceleration of the subject or a portion of the subject, pace, stride length, stride count and repetition count.

In one embodiment, the means for directly monitoring the orientation and movement of a subject includes at least one multi-function inertial sensor (e.g., 3-axis accelerometer or 3-axis gyroscope). As is well known in the art, orientation and motion of a subject can be readily determined from the signals or data transmitted by a multi-function inertial sensor.

According to the present invention, the accelerometer can be disposed in any anatomically appropriate position on subject 100. In one embodiment of the invention, an accelerometer (denoted "AC1" in FIG. 8) is disposed proximate the base of the sternum of subject 100.

In some embodiments, multiple accelerometers (or other means for monitoring orientation and/or movement of subject 100) may be positioned at various locations on the body of subject 100. Such positioning may allow for acquisition of data relating to motion of portions of the body of subject 100 relative to other portions of the body of subject 100, as well as relative to the environment.

In some embodiments, performance parameters including mental or emotional parameters such as, for example, stress or motivation level may be determined. Indications of such parameters can include, for example, trunk angle or foot strike characteristics, and can be monitored by the above-described means for monitoring orientation and/or movement of subject 100.

Data acquisition subsystem 20 can additionally include at least one additional physiological sensor (preferably a plurality of additional physiological sensors) adapted to monitor and record one or more physiological characteristics associated with monitored subject 100. The physiological sensors can include, without limitation, sensors that are adapted to monitor and record electrical activity of the brain, heart, and other muscles (e.g., EEG, ECG, EMG), pulse rate, blood oxygen saturation level (e.g., $SpO_2$), skin temperature, and core temperature. Physiological parameters measured and/or calculated may include, for example, heart rate, respiration rate, blood oxygen level, blood flow, hydration status, calories burned, muscle fatigue, and/or body temperature.

The additional sensors can, of course, be disposed in a variety of anatomically appropriate positions on a subject. By way of example, a first sensor (e.g., a pulse rate sensor) can be disposed proximate the heart of subject 100 to monitor pulse rate, and a second sensor (e.g., a microphone) can be disposed proximate the throat of subject 100 to monitor sounds emanating therefrom (e.g., sounds reflecting coughing).

Data acquisition subsystem 20 can also include one or more audio sensors, such as a microphone for monitoring sounds generated by monitored subject 100, and a speaker, to enable two-way communication by and between monitored subject 100 and a monitoring station or individual, such as, for example, an athletic trainer or medical personnel.

According to exemplary embodiments of the invention, the paired coils (e.g., electromagnetic coils 22a, 22b and 24a, 24b) and the aforementioned additional sensors can be positioned on or proximate subject 100 by various suitable means. Thus, the paired coils and/or additional sensors can, for example, be directly attached to subject 100 and/or can be included in a garment (e.g., athletic apparel) or accessory (e.g., watch, belt) worn by subject 100.

As set forth in U.S. Patent Application No. 61/275,633, filed Sep. 1, 2009, and co-pending U.S. patent application Ser. No. 12/869,627, filed Aug. 26, 2010, both of which are incorporated by reference herein in their entirety, the paired coils, additional sensors, processing and monitoring systems (e.g., local data units (LDUs) if employed), and associated wiring, cabling, and other power and signal transmission apparatuses and/or systems can also be embedded in or carried by a wearable garment or item that can be comfortably worn by a monitored subject.

U.S. Patent Application No. 61/275,576, filed Sep. 1, 2009, and co-pending U.S. patent application Ser. No. 12/869,576, filed Aug. 26, 2010, both of which are also incorporated by reference herein in their entirety, also disclose magnetometer-based wearable monitoring garments.

Control-Data Processing Subsystem

Control-data processing subsystem 40 includes programs, instructions, and associated algorithms and parameters to control data acquisition subsystem 20 and, hence, the paired electromagnetic coils (e.g., coils 22a, 22b, 24a, 24b, 32a, 32b, 34a, 34b) and the function thereof, and the transmission and receipt of coil transmissions (e.g., transmissions $T_{32}$, $T_{22}$, $T_{34}$, and $T_{24}$) as well as data transmission subsystem 50 and data monitoring subsystem 60. Such is discussed in detail below.

Control-data processing subsystem 40 is further programmed and adapted to retrieve and process coil transmissions or signals from the electromagnetic coils (e.g., coils 22a, 22b, 24a, 24b, 32a, 32b, 34a, 34b) in order to determine physiological information associated with monitored subject 100, to retrieve, process, and interpret additional signals transmitted by additional spatial parameter and physiological sensors (discussed below), and to transmit selective coil data, physiological and spatial parameters, physiological characteristics, and subject information to data monitoring subsystem 60 of the invention.

Control-data processing subsystem 40 further includes at least one "n-degrees-of-freedom" model or algorithm for determining at least one respiratory characteristic (e.g., $V_T$) from the retrieved coil transmissions or signals (e.g., measured displacements of the rib cage, abdomen, and chest wall).

Control-data processing subsystem 40 also preferably includes suitable algorithms that are designed and adapted to conduct multivariable analyses of data acquired by data acquisition subsystem 20 (e.g., coil transmissions and signals transmitted by additional spatial parameter and physiological sensors, as discussed below).

Control-data processing subsystem 40 also preferably includes suitable algorithms that are designed and adapted to determine respiratory characteristics, parameters, and statuses from measured multiple, interactive chest wall displacements. The algorithms are also preferably adapted to discount measured chest wall displacements that are associated with non-respiration movement (e.g., twisting of the torso) to enhance the accuracy of respiratory characteristic (and/or parameter) determinations.

Control-data processing subsystem 40 additionally preferably includes suitable programs, algorithms, and instructions to generate three-dimensional models of the chest wall of subject 100 from the measured multiple, interactive chest wall displacements.

Control-data processing subsystem 40 is also preferably programmed and adapted to determine additional and, in some instances, interrelated anatomical parameters, such as bending, twisting, coughing, etc., from the measured multiple, interactive chest wall displacements. In some instances, control-data processing subsystem 40 is programmed and adapted to compare retrieved coil transmissions reflecting measured chest wall displacements with stored selective combinations of coil transmissions and chest wall parameters that are associated therewith (e.g., "normal respiration and bending", "normal respiration and coughing").

By way of example, in one embodiment, a first chest wall parameter ($CWP_1$) defined as (or reflecting) "normal respiration and twisting of the torso" is stored in control-data processing subsystem 40. The coil transmissions and data associated with the first chest wall parameter ($CWP_1$) include transmissions $T_{32}$, $T_{22}$, $T_{34}$, and $T_{24}$ received by receive coil 24b that can represent displacements x, y, and z.

During monitoring of subject 100, similar coil transmissions may be received by receive coil 24b. Control-data processing subsystem 40 then compares the detected (or retrieved) transmissions to the stored transmissions and chest wall parameters associated therewith to determine (in real-time) the chest wall movement and, hence, respiratory activity based thereon; in this instance "normal respiration and twisting of the torso".

In some embodiments, the signals transmitted by the accelerometer (e.g., spatial parameter signals) are employed with the detected coil transmissions to determine and classify chest wall movement and associated respiratory activity of the monitored subject. In the noted embodiments, each stored chest wall parameter also includes spatial parameter signals associated with the chest wall parameter (e.g., normal respiration and twisting of the torso). Control-data processing subsystem 40 is adapted to compare retrieved coil transmissions and spatial parameter signals to the stored transmissions and spatial parameter signals, and the chest wall parameters associated therewith, to determine the chest wall movement and, hence, respiratory activity based thereon.

In some instances, control-data processing subsystem 40 is programmed and adapted to determine chest wall movement and respiratory activity based on retrieved coil transmissions, spatial parameter signals, and audio signals. In the noted embodiments, data acquisition subsystem 20 may also include an audio sensor, such as, for example, a microphone, that is disposed in an anatomically appropriate position on subject 100 (e.g., proximate the throat).

In this instance, each stored chest wall parameter also includes at least one audio parameter (e.g., >N db, based on the audio signal) that is associated with the chest wall parameter (e.g., normal respiration and coughing). Upon receipt of coil transmissions, spatial parameter signals, and audio signals, control-data processing subsystem 40 compares the retrieved coil transmissions, spatial parameter signals, and audio signals to the stored transmissions, spatial parameter signals, and audio parameters, and the chest wall parameters associated therewith, to determine the chest wall movement and respiratory activity based thereon (e.g., normal respiration and coughing).

Data Monitoring Subsystem

Data monitoring subsystem 60 is designed and adapted to receive and, in some embodiments, selectively monitor coil transmissions or signals (e.g., transmissions $T_{32}$, $T_{22}$, $T_{34}$, and $T_{24}$) and to display parameters associated therewith (e.g., displacement(s) along a selective axis), and/or to display a chest wall parameter (e.g., $CWP_1$), and/or to display a respiratory characteristic (e.g., $V_T$) or event. Such display can be via a variety of media, such as a personal digital assistant (PDA), a mobile phone, and/or a computer monitor, etc.

Data monitoring subsystem 60 is further preferably designed and adapted to display selective subject parameters, characteristics, information, and warnings or alarms. The data monitoring subsystem can also be adapted to display or broadcast data aurally. The aurally presented data can be voice messages, music, or other noises signifying an event. The data monitoring subsystem can be adapted to allow headphones or speakers to connect to the data monitoring subsystem, either wireless or wired, to display the aural data.

In some instances, data monitoring subsystem 60 is also adapted to receive and, in some embodiments, selectively monitor spatial parameter signals and signals transmitted by additional anatomical and physiological sensors (e.g., signals indicating skin temperature or $SpO_2$) and to display parameters and information associated therewith. The parameters can be associated with an athlete's physical activity. Physical or anatomical parameters measured and/or calculated may include, for example, time, location, distance, speed, pace, stride count, stride length, stride rate, and/or elevation. Physiological parameters measured and/or calculated may include, for example, heart rate, respiration rate, blood oxygen level, blood flow, hydration status, calories burned, muscle fatigue, and/or body temperature. In an embodiment, performance parameters may also include mental or emotional parameters such as, for example, stress level or motivation level. Mental and emotional parameters may be measured and/or calculated directly or indirectly either through posing questions to the athlete or by measuring things such as, for example, trunk angle or foot strike characteristics while running.

In some embodiments, data monitoring subsystem 60 includes a local electronic module or local data unit (LDU). By the term "local" as used in connection with a LDU, it is meant that the LDU is disposed close to the electromagnetic coils, such as on or in a wearable garment containing the coils (which is discussed in detail below). The LDU is preferably adapted to receive and monitor coil transmissions (or signals), preprocess the coil transmissions, and store the coil transmissions and related data.

In some embodiments, the LDU is also adapted to receive and monitor the spatial parameter transmissions (or signals) and additional signals transmitted by additional anatomical and physiological sensors (if employed), to preprocess the signals, and to store the signals and related data.

Data Transmission Subsystem

Data transmission subsystem 50 includes communication protocols to (i) transmit control signals to data acquisition subsystem 20, (ii) transmit coil transmissions (or signals) from the coils to control-data processing subsystem 40, and (iii) transmit data and information, including coil transmissions (or signals) and related parameters, physiological characteristics, spatial parameters, and subject information from control-data processing subsystem 40 to data monitoring subsystem 60.

In some embodiments, the communication link between data acquisition subsystem 20 and control-data processing subsystem 40 includes conductive wires or similar direct communication means. In some embodiments, the communication link between data acquisition subsystem 20 and control-data processing subsystem 40, as well as between control-data processing subsystem 40 and data monitoring subsystem 60, includes a wireless (or radio) link. The communication link between data acquisition subsystem 20 and control-data processing subsystem 40, and the communication link between control-data processing subsystem 40 and data monitoring subsystem 60 need not be the same type of link.

Approaches to radio communication of data may rely on continuous or regularly scheduled data transmission and typically employ one mode of radio transmission technology. In contrast, data transmission subsystem 20 of the present invention includes multimodal communications means, which enables effective communication to data monitoring subsystem 60 (or other desired device or system) to be acquired in a wide range of settings where a single radio mode would be ineffective.

In one embodiment of the invention, the multimodal communications means includes multiple radio subsystems. According to the invention, the radio subsystems can include multiple known systems, including, for example, Global System for Mobile Communications (GSM) and BlueTooth® systems.

In one embodiment, the multimodal communications means includes multiple-frequency radio transmissions. The frequencies can be steady state and/or random.

According to an exemplary embodiment of the invention, data transmission subsystem 50 may further include algorithms and programming to control the noted multimodal communications means. Such control may include preprogrammed transmission of signals (e.g., transmission when the characteristic represented by a signal is deemed relevant, transmission during particular periods of activity, or transmission according to a particular mode in response to feedback or a condition of another mode).

Multimodal communications according to the present invention can also allow for communication with a plurality of devices. For example, a product can communicate heart rate data to a first device using wireless sensor network technology, e.g., ANT+, and communicate speed data to a mobile phone using another wireless technology, e.g., Bluetooth Low Energy.

Using multimodal communications can allow for optimization of system performance. For example, data-intense transmissions, e.g., a detailed heart rate signal, can be sent via a first transmission standard or frequency capable of handling large amounts of data. Simpler transmission, e.g., speed/distance data points, can be sent via a second transmission standard or frequency that may require less power or provide other benefits over the first transmission standard.

As indicated above, it is to be understood that the present invention is not limited to the systems and associated methods described herein. Indeed, according to the invention, the multimodal communications means of the invention can be employed with various physiological and/or anatomical monitoring systems and methods, including the systems and methods referenced above.

As will readily be appreciated by one having ordinary skill in the art, the multimodal communications means in conjunction with the real-time signal acquisition and processing capabilities discussed above creates a "smart" communications structure that maximizes battery efficiency, ensures connectivity across a range of environments, and enables data to be transmitted only when relevant.

Yet another advantage of the invention is the use of multimodal communications means in conjunction with monitoring systems that allow for measurement of front to back separation between magnetometers as well as vertical separation between different sets of magnetometers. This allows the system to separate a desired signal and information from motion artifacts caused by ambulatory motion.

Additional advantages and applications of the present invention are apparent with reference to the systems and methods disclosed in U.S. patent application Ser. No. 12/869,578, filed Aug. 26, 2010, U.S. patent application Ser. No. 12/869,582, filed Aug. 26, 2010, U.S. patent application Ser. No. 12/869,576, filed Aug. 26, 2010, U.S. patent application Ser. No. 12/869,585, filed Aug. 26, 2010, U.S. patent application Ser. No. 12/869,627, filed Aug. 26, 2010, U.S. patent application Ser. No. 12/869,625, filed Aug. 26, 2010, and U.S. patent application Ser. No. 12/869,586, filed Aug. 26, 2010, each of which is incorporated by reference herein in its entirety.

Without departing from the spirit and scope of this invention, one of ordinary skill can make various changes and modifications to the invention to adapt it to various usages and conditions. As such, these changes and modifications are properly, equitably, and intended to be, within the full range of equivalence of the invention.

What is claimed is:

1. A system for transmitting information about a subject engaged in a physical activity, the system comprising:
a data acquisition subsystem carried on a subject's body, wherein the data acquisition subsystem is configured to monitor the subject and generate a first signal representative of a parameter of the subject; and
a data transmission subsystem configured to transmit the first signal from the data acquisition subsystem to a data monitoring subsystem,
wherein the data transmission subsystem has a first transmission mode and a second transmission mode for transmitting the first signal,
wherein the data transmission subsystem is configured to transmit the first signal using either of the first transmission mode and the second transmission mode,
wherein the data transmission subsystem is configured to transmit the first signal via one of the first transmission mode and the second transmission mode in response to a condition of the other of the first transmission mode and the second transmission mode; and
wherein the first transmission mode comprises a radio transmission according to a first frequency and the second transmission mode comprises a radio transmission according to a second frequency.

2. The system of claim 1, wherein the first transmission mode includes steady state frequencies.

3. The system of claim 1, wherein the second transmission mode includes random frequencies.

4. The system of claim 2, wherein the second transmission mode includes steady state frequencies.

5. The system of claim 3, wherein the first transmission mode includes random frequencies.

6. The system of claim 1, wherein the data transmission subsystem is further configured to transmit the first signal from the data acquisition subsystem to the data monitoring subsystem via a data processing subsystem.

7. The system of claim 6, wherein the data processing subsystem is configured to process the first signal to obtain a physiological parameter of the subject, and wherein the data transmission subsystem is configured to transmit the physiological parameter from the data processing subsystem to the data monitoring subsystem.

8. The system of claim 6, wherein the data processing subsystem is configured to process the first signal to determine a performance parameter of the subject and wherein the data transmission subsystem is configured to transmit the performance parameter from the data processing subsystem to the data monitoring subsystem.

9. The system of claim 6, wherein the data processing subsystem is configured to process the first signal to obtain a respiratory parameter of the subject and wherein the data transmission subsystem is configured to transmit the respiratory parameter from the data processing subsystem to the data monitoring subsystem.

10. The system of claim 6, wherein the data processing subsystem is configured to process the first signal to obtain a spatial parameter of the subject and wherein the data transmission subsystem is configured to transmit the spatial parameter from the data processing subsystem to the data monitoring subsystem.

11. The system of claim 1, wherein the data transmission subsystem is configured to determine if the first signal is relevant, and to transmit the first signal only when the first signal is determined to be relevant.

12. The system of claim 1, wherein the data transmission subsystem is configured to transmit the first signal during particular periods of activity.

13. The system of claim 1, wherein the first transmission mode and the second transmission mode comprise modes compatible with at least one of Global System for Mobile Communications and BlueTooth® systems.

14. The system of claim 1, wherein the data acquisition subsystem comprises a sensor, the sensor being positioned on a garment worn by the subject and being configured to generate the first signal.

15. The system of claim 1, wherein the data acquisition subsystem includes a first magnetometer and a second magnetometer, wherein the first and second magnetometers are responsive to changes in distance therebetween, and wherein the first signal contains information regarding the distance between the first magnetometer and the second magnetometer.

16. The system of claim 1,
wherein the data transmission subsystem is configured to transmit the signal using the second transmission mode based on feedback of the first transmission mode.

17. A method for transmitting information about a subject engaged in a physical activity, the method comprising:
generating a first signal with a data acquisition subsystem, wherein the first signal contains information representing a first parameter of the subject;
generating a second signal with a data acquisition subsystem, wherein the second signal contains information representing a second parameter of the subject,
transmitting the first signal using a first transmission standard, wherein the first signal is transmitted by a data transmission subsystem to a data monitoring subsystem; and
transmitting the second signal using a second transmission standard, wherein the second transmission standard is different from the first transmission standard, and wherein the second signal is transmitted by the data transmission subsystem to the data monitoring subsystem, wherein:
the second transmission standard requires less power than the first transmission standard,
the first signal is transmitted via a first transmission mode in response to a condition of a second transmission mode, and
the second signal is transmitted via the second transmission mode in response to a condition of the first transmission mode.

18. The method of claim 17, wherein the first transmission standard includes steady state frequencies.

19. The method of claim 18, wherein the second transmission standard includes random frequencies.

20. The method of claim 17, wherein the first transmission standard includes random frequencies.

21. The method of claim 20, wherein the second transmission standard includes steady state frequencies.

22. The method of claim 17 further comprising processing the first signal and the second signal with a data processing subsystem, wherein transmitting the first signal and the second signal to the data monitoring subsystem comprises transmitting the first signal and the second signal to the data monitoring subsystem via the data processing subsystem.

23. The method of claim 22 further comprising processing the first signal with the data processing subsystem to obtain a physiological parameter of the subject.

24. The method of claim 22 further comprising processing the first signal with the data processing subsystem to obtain a performance parameter of the subject.

25. The method of claim 22 further comprising processing the first signal with the data processing subsystem to obtain a respiratory parameter of the subject.

26. The method of claim 22 further comprising processing the first signal with the data processing subsystem to obtain a spatial parameter of a subject.

27. The method of claim 17, wherein the first transmission standard comprises a radio transmission according to a first frequency and the second transmission standard comprises a radio transmission according to a second frequency.

28. The method of claim 17, wherein the data acquisition subsystem includes a first magnetometer and a second magnetometer, wherein the first and second magnetometers are responsive to changes in distance therebetween, and wherein the first signal is representative of the distance between the first magnetometer and the second magnetometer.

29. The system of claim 17, wherein the first parameter is a physiological parameter and the second parameter is a spatial parameter.

30. The method of claim 17, wherein the first signal is a heart rate signal,
wherein the second signal is a speed signal,
wherein the first transmission standard is an ANT standard, and
wherein the second transmission standard is a Bluetooth Low Energy standard.

* * * * *